(12) United States Patent
Hedberg (10) Patent No.: US 10,251,775 B2
(45) Date of Patent: Apr. 9, 2019

(54) LOW HUMIDITY DEVICE FOR BODY JOINT THERAPY

(76) Inventor: Mary Lucia Leone Hedberg, North Attleboro, MA (US)

( * ) Notice: Subject to any disclaimer, the term of this patent is extended or adjusted under 35 U.S.C. 154(b) by 1299 days.

(21) Appl. No.: 12/252,001

(22) Filed: Oct. 15, 2008

(65) Prior Publication Data

US 2009/0099488 A1    Apr. 16, 2009

Related U.S. Application Data

(60) Provisional application No. 60/999,003, filed on Oct. 15, 2007.

(51) Int. Cl.
*A61F 5/00* (2006.01)
*A61F 7/02* (2006.01)
*A61F 7/00* (2006.01)

(52) U.S. Cl.
CPC ........ *A61F 7/02* (2013.01); *A61F 2007/0032* (2013.01); *A61F 2007/026* (2013.01); *A61F 2007/0249* (2013.01)

(58) Field of Classification Search
CPC .... A61F 15/004; A61F 13/041; A61F 13/043; A41D 13/08; A41D 27/10; A41B 7/12
USPC ...... 601/151–153, 166, 1, 11, 15, 150; 2/16, 2/18–24, 2.16, 59, 69.5, 125, 126, 158, 2/159, 161.1, 161.4, 161.6–161.8; 607/96, 108, 111, 114; 602/3
See application file for complete search history.

(56) References Cited

U.S. PATENT DOCUMENTS

| | | | | |
|---|---|---|---|---|
| 1,577,630 A * | 3/1926 | Yerger | ............................... | 2/59 |
| 3,189,919 A * | 6/1965 | Chase | .................. | A41D 13/065 |
| | | | | 128/892 |
| 3,657,741 A * | 4/1972 | Blanco | ............................... | 2/59 |
| 3,741,203 A * | 6/1973 | Liman | ............................... | 602/3 |
| 3,889,684 A * | 6/1975 | Lebold | ...................... | A61F 7/02 |
| | | | | 607/109 |
| 4,036,220 A * | 7/1977 | Bellasalma | ....................... | 602/3 |
| 4,274,158 A * | 6/1981 | Pogorski et al. | .................. | 2/2.16 |
| 4,308,864 A * | 1/1982 | Small | ...................... | A61F 13/06 |
| | | | | 128/850 |
| 4,530,350 A * | 7/1985 | Brown et al. | ...................... | 602/3 |
| 4,662,006 A * | 5/1987 | Ross, Jr. | ............................ | 2/158 |
| 4,749,392 A * | 6/1988 | Aoki et al. | .......................... | 96/6 |
| 4,856,112 A * | 8/1989 | Effle | ...................... | A41D 13/08 |
| | | | | 2/16 |
| 4,899,749 A * | 2/1990 | Laroco | ...................... | A61F 7/08 |
| | | | | 383/901 |
| 4,951,666 A * | 8/1990 | Inman | ..................... | A61F 7/103 |
| | | | | 383/111 |

(Continued)

OTHER PUBLICATIONS

AccuWeather Arthritis Index; http://cortex/accuweather.com/adc2004/pub/images/products_services/Newspaper/no_71/gif; circa 2007.

(Continued)

*Primary Examiner* — Michael J Tsai
*Assistant Examiner* — Christopher E Miller
(74) *Attorney, Agent, or Firm* — Fish & Richardson P.C.

(57) ABSTRACT

A self-contained appliance for passive therapy of arthritis discomfort in a bone joint, including a bone joint encompassing element formed of a moisture impermeable barrier material and defining a therapy region about one or more bone joints, and a desiccative agent disposed within the therapy region.

20 Claims, 10 Drawing Sheets

(56) References Cited

U.S. PATENT DOCUMENTS

| | | | | | |
|---|---|---|---|---|---|
| 5,005,215 | A | * | 4/1991 | McIlquham | A41D 13/001 119/654 |
| 5,037,459 | A | * | 8/1991 | Spruill et al. | 96/118 |
| 5,173,967 | A | * | 12/1992 | Carter | 2/242 |
| 5,179,944 | A | * | 1/1993 | McSymytz | 607/114 |
| 5,230,333 | A | * | 7/1993 | Yates et al. | 607/111 |
| 5,328,449 | A | * | 7/1994 | Andrews et al. | 602/42 |
| 5,345,609 | A | * | 9/1994 | Fabry et al. | 2/20 |
| 5,466,251 | A | * | 11/1995 | Brunson et al. | 607/112 |
| 5,542,121 | A | * | 8/1996 | Lahaussois et al. | 2/59 |
| 5,542,191 | A | * | 8/1996 | Shouse et al. | 34/104 |
| 5,592,953 | A | * | 1/1997 | Delao | 128/882 |
| 5,643,183 | A | * | 7/1997 | Hill | 602/3 |
| 5,720,713 | A | * | 2/1998 | Hutchison | A61F 13/041 128/849 |
| 5,815,948 | A | * | 10/1998 | Dzielak | A41D 17/00 2/22 |
| 5,817,038 | A | * | 10/1998 | Orange | A61F 13/041 602/3 |
| 5,832,539 | A | * | 11/1998 | Williams | 2/239 |
| 5,840,080 | A | * | 11/1998 | Der Ovanesian | A61F 7/02 607/112 |
| 6,041,443 | A | * | 3/2000 | Pas et al. | 2/239 |
| 6,092,235 | A | * | 7/2000 | Santa Cruz et al. | 2/16 |
| 6,145,155 | A | | 11/2000 | James et al. | |
| 6,210,352 | B1 | * | 4/2001 | Williams et al. | 602/3 |
| 6,317,889 | B1 | * | 11/2001 | Reilly et al. | 2/24 |
| 6,328,761 | B1 | * | 12/2001 | Ueki | 607/111 |
| 6,378,224 | B1 | * | 4/2002 | Qualkinbush et al. | 34/80 |
| 6,514,279 | B1 | * | 2/2003 | Lavin, Jr. | 607/108 |
| 6,560,784 | B2 | * | 5/2003 | Hill | 2/171 |
| 6,916,301 | B1 | * | 7/2005 | Clare | A61F 15/004 128/856 |
| 7,141,122 | B2 | * | 11/2006 | McKenzie | 134/6 |
| 7,290,290 | B2 | * | 11/2007 | Treadway Fancher | 2/16 |
| 7,913,320 | B2 | * | 3/2011 | Grissom | A61M 25/02 2/59 |
| 8,117,677 | B2 | * | 2/2012 | Toth | 2/413 |
| 8,529,481 | B1 | * | 9/2013 | Lois | A61F 5/01 602/3 |
| 8,535,295 | B2 | * | 9/2013 | Palma | A61F 13/043 602/3 |
| 2003/0145367 | A1 | * | 8/2003 | Isom et al. | 2/159 |
| 2003/0163071 | A1 | * | 8/2003 | Cominsky | 602/41 |
| 2003/0191424 | A1 | * | 10/2003 | Skinner | A61F 15/004 602/62 |
| 2004/0013713 | A1 | | 1/2004 | Berry et al. | |
| 2005/0020949 | A1 | * | 1/2005 | Switzer | A61F 15/008 602/3 |
| 2005/0177965 | A1 | * | 8/2005 | Edoh | 15/160 |
| 2006/0004427 | A1 | * | 1/2006 | Wilson | A61F 7/02 607/108 |
| 2006/0276734 | A1 | * | 12/2006 | Satkowiak | 602/3 |
| 2007/0083163 | A1 | * | 4/2007 | Rydell | A61M 25/02 604/174 |
| 2007/0088281 | A1 | * | 4/2007 | Ritchey | 604/174 |
| 2007/0101479 | A1 | * | 5/2007 | Turner | 2/159 |
| 2007/0106356 | A1 | * | 5/2007 | Carstens | 607/112 |
| 2007/0163027 | A1 | * | 7/2007 | Hamilton | 2/171 |
| 2007/0193066 | A1 | * | 8/2007 | Baychar | 36/55 |
| 2008/0092262 | A1 | | 4/2008 | James Carr | |
| 2008/0168593 | A1 | * | 7/2008 | Parker | 2/167 |
| 2008/0172767 | A1 | | 7/2008 | Friedstrom | |
| 2008/0229476 | A1 | | 7/2008 | Sanders | |
| 2008/0216218 | A1 | * | 9/2008 | McKinney et al. | 2/457 |
| 2009/0000003 | A1 | * | 1/2009 | Hinebaugh | 2/16 |

OTHER PUBLICATIONS

Arthritis; Http://www.arthritis.org/disease-center.php?disease_icd-31&df-definition; circa 2007.

Barometer; http://www.en.wikipedia.org/wiki/Barometer; Oct. 11, 2007.

Does Weather Affect Arthritis Pain?; http://www.johnshopkinshealthalerts.com/reports/arthritis/44-1.html; Dec. 6, 2007.

Eustice, Carol and Richard; Is There a Connection Between Weather and Arthritis Symptoms?; http://arthritis.about.com/od/weather/f/weather.htm; Jan. 28, 2008.

Freeman, David; Does Weather really Affect Arthritis?; http://searchwarp.com/swa256298.htm; Dec. 14, 2007.

Gorman, T.; What are your choices for Arthritis Relief?; http://ezinearticles.com/?What-Are-Your-Choices-For-Arthritis-Relief?id-427510; circa 2007.

Grossman, K.; Weather and Arthritis-Barometric Pressure Affect; http://arthritis.about.com/od/weather/Weather_Arthritis_Barometric_Pressure_Affect_Humidity_climate.htm; Sep. 10, 2007.

Harlfinger, O.; Weather-induced effects on pain perception; Fortschritte der Medizin; vol. 109, No. 32; pp. 647-650; Nov. 10, 1991.

Heat, Humidity, and Gout; Johns Hopkins Health Alerts; http://www.johnshopkinshealthalerts.com/alerts/JohnsHopkinsHealthAlertsArthritis; Nov. 5, 2007.

Jamison, Robert N., Karen O. Anderson, and Mark A. Slater; Weather changes and pain: perceived influence of local climate on pain complaint in chronic pain patients; Pain, vol. 6, No. 2; pp. 309-315; May 1995.

Kamhi, Ellen and Eugene R. Zampieron; Arthritis; Berkeley: Celestial Arts; pp. 295-320; 2006.

Katzenstein, Larry; Taking Charge of Arthritis; New York: Reader's Digest Association; pp. 172-199; 2001.

Living with Arthritis; http://arthritisinsight.com/living/; Oct. 15, 2007.

Maddox, George L. ed.; The Encyclopedia of Aging; New York: Springer Publishing Company; pp. 91-92; 2001.

Marieb, E.N.; Essentials of Human Anatomy & Physiology; Boston: Benjamin Cummings; pp. 149-155; 2003.

Rheumatoid Arthritis—Cause; http://www.webmd.com/rheumatoid-arthritis/tc/rheumatoid-arthritis-cause; Nov. 2, 2007.

Ng, Jennifer, David Scott, Ashish Taneja, Peter Gow, and Asmita Gosai; Weather changes and pain in rheumatology patients; APLAR Journal of Rheumatology; vol. 7, No. 3, pp. 204-206; Nov. 2004.

Seeds, W.; Does the Weather Affect Your Arthritis Joint Pain?; http://www.allaboutarthritis.com/AllAboutArthritis/layoutTemplates/html/en/contentdisplay/document/condition/arthritis/generalArticle/wearther_arthritis_pain.htm; Apr. 3, 2007.

Sibley, J.T.; Weather and arthritis symptoms; Journal of Rheumatology; vol. 12, Issue 4; pp. 707-710; 1985.

Theodosakis, Jason, Brenda Adderly, and Barry Fox; The Arthritis Cure; New York: St. Martin's Press; pp. 53-68; 1997.

Weather and Arthritis; http://www.midwestarthritis.com/html/weather_arthritis.htm; Sep. 27, 2007.

* cited by examiner

LOW HUMIDITY DEVICE FOR BODY JOINT THERAPY

RELATED APPLICATION

This application claims priority to U.S. Provisional Patent Application No. 60/999,003 titled "Device and Method for Relief of Arthritis Pain Symptoms," filed on Oct. 15, 2007. The complete disclosure of the above application is incorporated herein by reference.

BACKGROUND

This disclosure relates to low humidity devices for body joint therapy.

Arthritis refers to an inflammation of the bone joints of a person or animal. Several forms of arthritis have been identified, and their causes may range from genetics to intense activity sports. Arthritis often appears in hips, knees, hands, or wrists and results in chronic pain and varying degrees of disability.

SUMMARY

In general, in one aspect, a self-contained appliance for passive therapy of arthritis discomfort in a bone joint includes a bone joint encompassing element formed of a moisture impermeable barrier material and defining a therapy region about one or more bone joints, and a desiccative agent disposed within the therapy region.

Implementations may include one or more of the following features. One or more closure elements associated with the bone joint encompassing element engage about a body limb associated with the one or more bone joints, thereby containing the therapy region in relative isolation from an external environment. In some examples, the one or more bone joints are joints of the fingers, hand and/or wrist, the bone joint encompassing element has a general shape of a mitt, and the one or more closure elements associated with the bone joint encompassing element are in engagement about a wearer's wrist or forearm; or the one or more bone joints are joints of the toes, foot and/or ankle, the bone joint encompassing element has a general shape of a bootie or sock, and the one or more closure elements associated with the bone joint encompassing element are in engagement about a wearer's ankle or calf. In some examples, the one or more bone joints is a bone joint of a body limb, the bone joint encompassing element has a general shape of a sleeve, and the one or more closure elements associated with the bone joint encompassing element are in engagement about a wearer's limb above and below the joint. An axial closure element releasably joins opposed, axially-extending edge regions of the sleeve for securing the body encompassing element in engagement about the body limb. The axial closure element can be, for example, zippers or hook-and-loop type fasteners. In some examples, the bone joint of a limb is a knee, and the one or more closure elements are in engagement about a wearer's upper leg and lower leg. In some examples, the bone joint of a limb is an elbow, and the one or more closure elements are in engagement about a wearer's upper arm and lower arm. The self-contained appliance for passive therapy of arthritis discomfort in a bone joint includes a moisture permeable inner liner, and the desiccative agent is disposed between the moisture impermeable barrier material and the moisture permeable inner liner. The inner liner is attached to the moisture impermeable barrier material to form one or more compartments to accommodate the desiccant agent. The desiccant agent can be, for example, silica gel. The moisture impermeable barrier material includes a thermal insulator to retain heat within the appliance.

In general, in another aspect, a method for passive therapy of arthritis discomfort in a bone joint includes the steps of enclosing one or more bone joints within a therapy region of a self-contained treatment appliance, the therapy region being defined by a bone joint encompassing element formed of a moisture impermeable barrier material; placing a desiccative agent within the therapy region; securing one or more closure elements in engagement about a body limb associated with the one or more bone joints, for containing the therapy region in relative isolation from an external environment; and continuing the therapy for a period of time.

Implementations may include one or more of the following features. The method includes the further step of proceeding with normal movements and activities during therapy.

In general, in another aspect, a hand encompassing element includes a moisture impermeable outer shell and a moisture permeable inner liner to form a first compartment for accommodating a wearer's hand and a second compartment for accommodating a desiccant material, the first and second compartments being separated by the moisture permeable inner liner to allow moisture from the first compartment to permeate to the second compartment and be adsorbed by the desiccant material. A closure element associated with the hand encompassing element engages about the wearer's wrist or forearm.

These and other aspects and features, and combinations of them, may be expressed as methods, apparatus, appliances, systems, means for performing functions, program products, and in other ways.

Advantages of the aspects, apparatuses, appliances, and methods may include one or more of the following. Discomfort due to arthritis joint can be reduced. The appliance for therapy of arthritis discomfort is passive and entirely self contained, e.g., the appliance does not require connection to an electric outlet, so the appliance is safe for use when the wearer is asleep. The appliance is simple and easy to use. The manufacturing cost of the appliance is low.

The details of one or more embodiments of the subject matter described in this disclosure are set forth in the accompanying drawings and the description below. Other features, aspects, and advantages of the subject matter will become apparent from the description, the drawings, and the claims.

DETAILED DESCRIPTION

Like reference numbers and designations in the various drawings indicate like elements.

The following describes examples of self-contained appliances for passive therapy of arthritis discomfort in one or more joints of a wearer's body. The self-contained appliance includes a body joint encompassing element that defines a therapy region about one or more body joints, and a desiccative agent is disposed within the therapy region to reduce the moisture content in the therapy region. One or more closure elements associated with the body joint encompassing element engage about a body limb associated with the one or more body joints, thereby containing the therapy region in relative isolation from an external environment. For example, a mitten or a flexible sleeve made of a moisture impermeable barrier material can be used to cover or encompass a person's hand or joint region of a limb with adjustable fasteners at each opening so as to prevent external atmospheric moisture from contacting the skin in the region of the painful joint. The mitten or sleeve can contain, e.g., can be lined with, a desiccative agent, for example, dried silica-gel or other hydroscopic material to reduce moisture in the mitten or sleeve (e.g., atmospheric moisture encompassed within or entering the therapy region, or moisture emanating from the skin (perspiration) while the mitten or sleeve is being worn).

Figure 1:
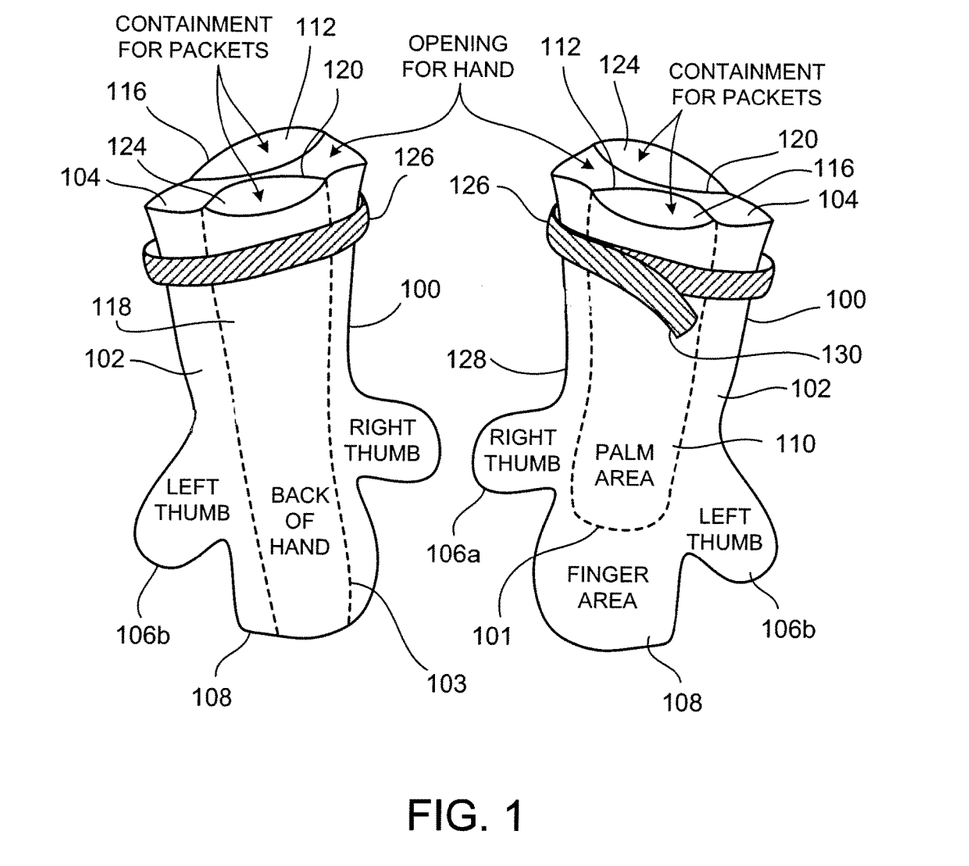
FIG. 1 is a perspective view of an example pair of low-humidity mittens.

FIG. 1 is a perspective view of an example pair of low-humidity mittens 100 that can be used for therapy to treat arthritis discomfort or pain in the joints of hands and wrists of some users. Each low-humidity mitten 100 includes a hand-encompassing member 102 that is shaped and sized to accommodate the hand and wrist of a user to create a low humidity environment in the region about the hand and wrist. The hand-encompassing member 102 may include an outer shell and an inner liner. The outer shell may be made of a moisture impermeable barrier material, such as a moisture impermeable fabric such as urethane-coated polyester, as commonly used in the ground-contact sections of camping tents. The inner liner can be made of a moisture permeable fabric that is soft and comfortable to the skin. For example, the inner liner can include moisture wicking fabric that wicks perspiration away from the skin and leaves the moisture on the side of the fabric facing desiccant packets described below. The low-humidity mitten 100 has a shape similar to a cooking mitten and can be worn comfortably for several hours.

The hand-encompassing member 102 includes an opening 104 for receiving the hand and wrist of the user. The hand-encompassing member 102 defines a therapy region, such as a hand compartment 128 for accommodating the user's hand. The hand compartment 128 defines a right thumb compartment 106a for receiving the right thumb and a finger compartment 108 for receiving the other four fingers of the right hand. In some examples, the mitten 100 is designed for use on either the right hand or left hand, and includes a left thumb compartment 106b for receiving the left thumb when worn on the left hand. When the mitten 100 is worn on either hand, the empty thumb compartment can be tucked into the mitten 100.

On one side of the mitten 100, the inner liner and the outer shell may be sewn along dashed lines 101 to form a palm compartment 110 for accommodating desiccant packets, such as packets of silica gel, for adsorbing moisture from the hand compartment 128. An opening 116 allows easy insertion and removal of the desiccant packets from the palm side of the mitten. The moisture permeable inner liner 112 allows moisture from the hand (e.g., palm region of hand) to pass to the palm compartment 110 and be adsorbed by the desiccant packet contained therein.

On another side of the mitten 100, the inner liner and the outer shell may be sewn along dashed lines 103 to form a back-of-hand compartment 118 for accommodating desiccant packets, such as packets of silica gel, for adsorbing moisture from the back of the user's hand. An opening 124 allows easy insertion and removal of the desiccant packets on the back side of the mitten. The moisture permeable liner 120 allows moisture from the hand (e.g., back of hand) to pass to the back-of-hand compartment 118 and be adsorbed by the desiccant packet therein.

In this example, the back-of-hand compartment 118 extends to the finger area 108, whereas the palm compartment 110 does not extend to the finger area 108. This provides more ability for the wearer to manipulate and feel objects with the fingers when wearing the low-humidity mitten 100.

The low-humidity mitten 100 includes, for example, an elastic strap or closure element 126 that goes around a wrist portion of the hand-encompassing member 102 and has cooperating hook-and-loop-type fasteners 130. After the user inserts his or her hand into the hand-encompassing member 102 through the opening 104, the elastic strap 126 can be tightened to seal off (or reduce) the remaining openings between a cuff area of the hand-encompassing member 100 and the user's wrist (or forearm, if the mitten 100 has a long sleeve). The drying agents in the palm compartment 110 and the back-of-hand compartment 118 adsorb moisture in the hand compartment 128, forming a low humidity environment in the vicinity of the user's hand and wrist.

In some implementations, the desiccant can be sewn into the palm compartment 110 and the back-of-hand compartment 118 to form an integrated mitten. The moisture permeable inner liners 112 and 120 can be sewn to the outer shell to form quilted sections each containing desiccant such as silica gel. For example, to regenerate the silica gel, the user can flip the mitten inside-out and place the moisture-saturated mitten in a clothes dryer or other low or ultra-low humidity environment, e.g., as described below.

In some implementations, the impermeable outer shell can include insulation to promote the retention of heat by the enclosure. Some arthritis sufferers report that application of heat to an afflicted bone joint helps relieve pain. The heat source may be the process used to dry the desiccant material. The insulation will slow the loss of heat from the desiccant material and also cause body heat to be retained by the enclosure.

In some examples, application of low humidity to afflicted joints for several hours each day can effectively reduce arthritis pain. For example, wearing the low-humidity mitten 100 during normal sleeping hours may be sufficient to reduce arthritis discomfort. The user can regenerate the drying agents (e.g., silica gel) each day to a dry state using, for example, a clothes dryer at conventional setting, a conventional oven set to less than about 200° F., or a microwave oven set to low power. In each case, the drying temperature should preferably be similar to the boiling point of water, but not so high that the mitten fabric or dessicant pouch material is damaged or degraded.

Figures 2A, 2B:
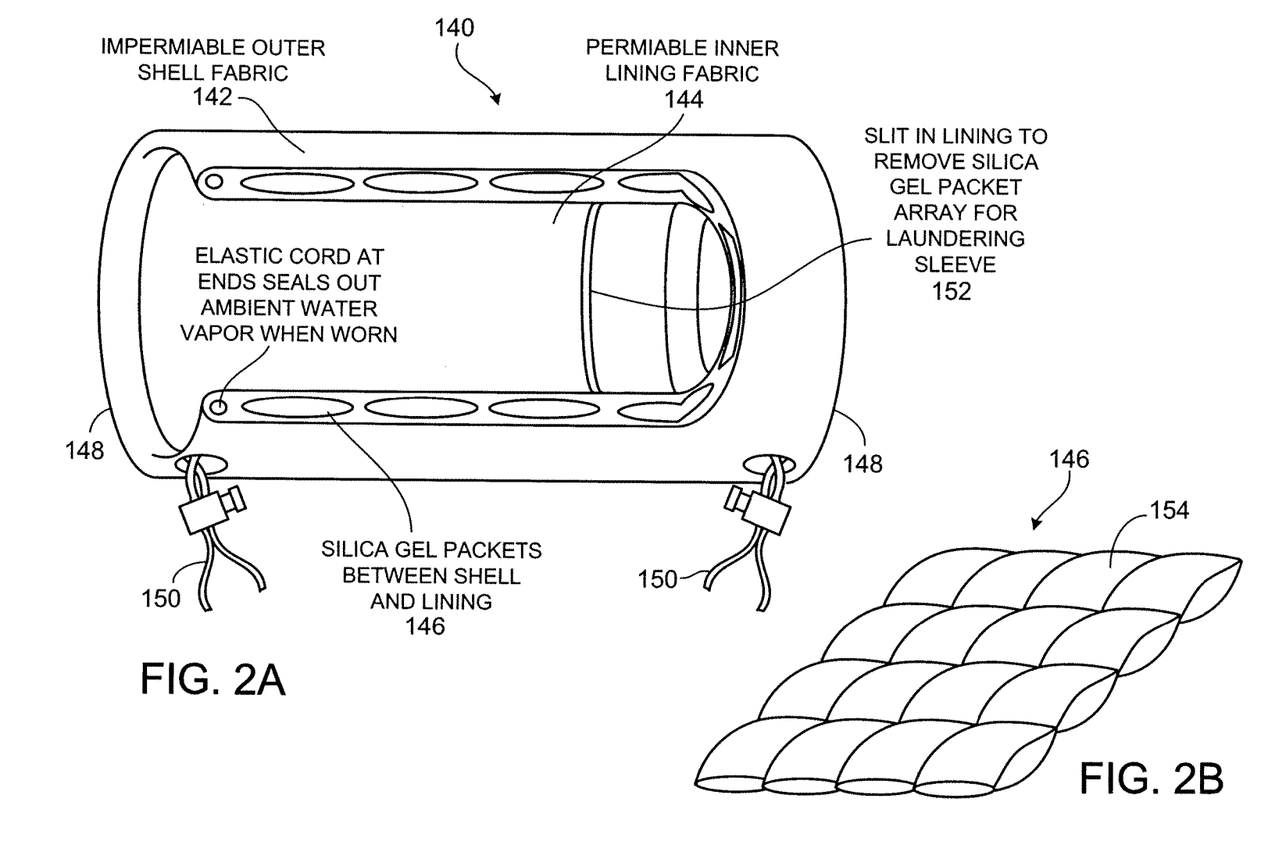
FIG. 2A shows an example low-humidity sleeve (with two ends open).
FIG. 2B shows an example packaging of drying agents.

FIG. 2A is an example low-humidity sleeve 140 for limb joint (e.g., elbow joint or knee joint). The low-humidity sleeve 140 includes a moisture impermeable outer shell fabric 142 and a moisture permeable inner lining fabric 144.

Drying agents 146, such as packets of silica gel, are placed in the space between the outer shell 142 and the inner liner 144. At each end 148 of the sleeve 140 is a drawstring or closure element 150 that can be pulled tight to close the opening at each end 148 after the sleeve 140 has been pulled over the limb bone joint. The moisture permeable inner lining fabric 144 allows moisture in the sleeve 140 (e.g., atmospheric moisture originally encompassed within the region of the sleeve 140 and moisture emanating from the user's skin (perspiration)) to permeate to and be adsorbed by the drying agents 146. The moisture impermeable outer shell fabric 142 prevents outside atmospheric moisture from entering the sleeve 140, thus permitting the desiccant to maintain the driest environment possible within the region of the sleeve for the longest time possible.

A slit 152 is provided in the moisture permeable inner lining fabric 144 to allow easy insertion and removal of the drying agents 146 to and from the space between the moisture impermeable outer shell fabric 142 and the moisture permeable inner lining fabric 144. In some implementations of sleeve 140 or mitten 100, provision is made for removing the desiccant packets to perform the process of regeneration of the desiccant's water-adsorbing capability. In other implementations, the desiccant packets remain in the sleeve or mitten, which is then turned inside out to present the moisture permeable fabric to the outside for increased speed and efficiency of desiccant regeneration.

FIG. 2B shows an example packaging of drying agents 146, such as silica gel. The drying agents are stored in several compartments 154 to prevent bunching of the silica gel. The length and width of the packaging 146 can be comparable to the size of the sleeve 140 so that the package of drying agents 146 fits in the space between the outer shell 142 and the inner lining 144.

The packaging of drying agents 146 shown in FIG. 2B can also be used for the low-humidity mitten 100 of FIG. 1. In this case, the dimensions of the drying agent package 146 are designed to match those of the palm compartment 110 and the back-of-hand compartment 118.

Figure 3:
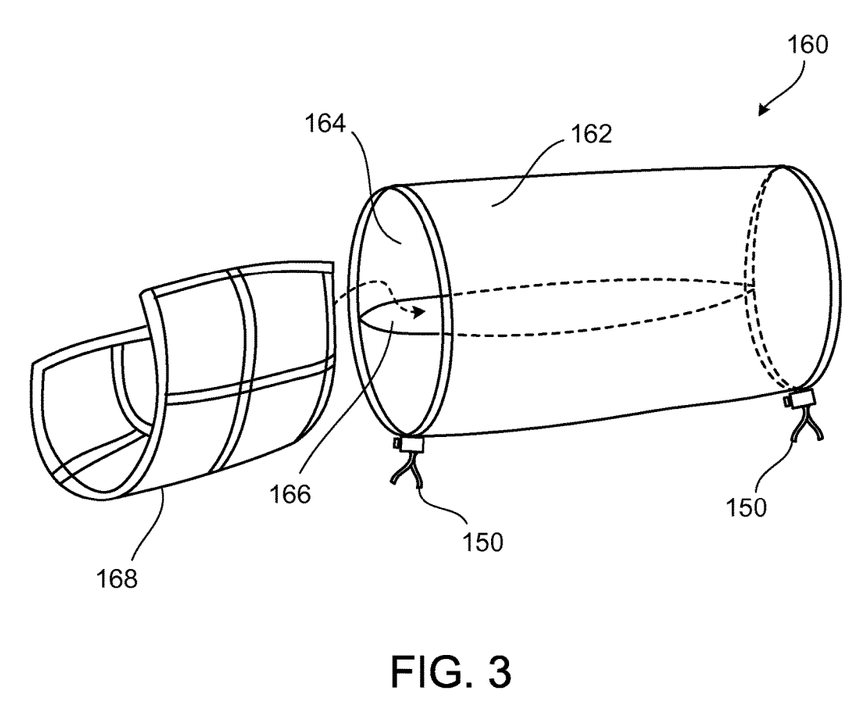
FIGS. 3, 4, and 5A show examples of low-humidity sleeves.

FIG. 3 shows an example low-humidity sleeve 160 that includes a moisture impermeable outer shell fabric 162 and a moisture permeable inner lining fabric 164. The outer shell 162 has a generally tubular shape. The inner lining fabric 164 includes an opening 166 to allow insertion and removal of a strip of desiccant packets 168, which can include silica gel. When using the sleeve 160, the strip of desiccant packets 168 lay flat around the space between the outer shell 162 and the inner liner 164. Drawstrings 150 can be pulled tight to close the openings at the ends of the sleeve 160 to maximize the ability of the desiccant to achieve and maintain lower humidity with the sleeve.

The moisture permeable inner lining fabric 164 allows moisture in the sleeve 160 to permeate to and be adsorbed by the desiccant in the desiccant packets 168. The moisture impermeable outer shell 162 prevents outside atmospheric moisture from entering the sleeve 160, interfering with the ability of the desiccant to achieve a low humidity environment in the region about the bone joint.

Figure 4:
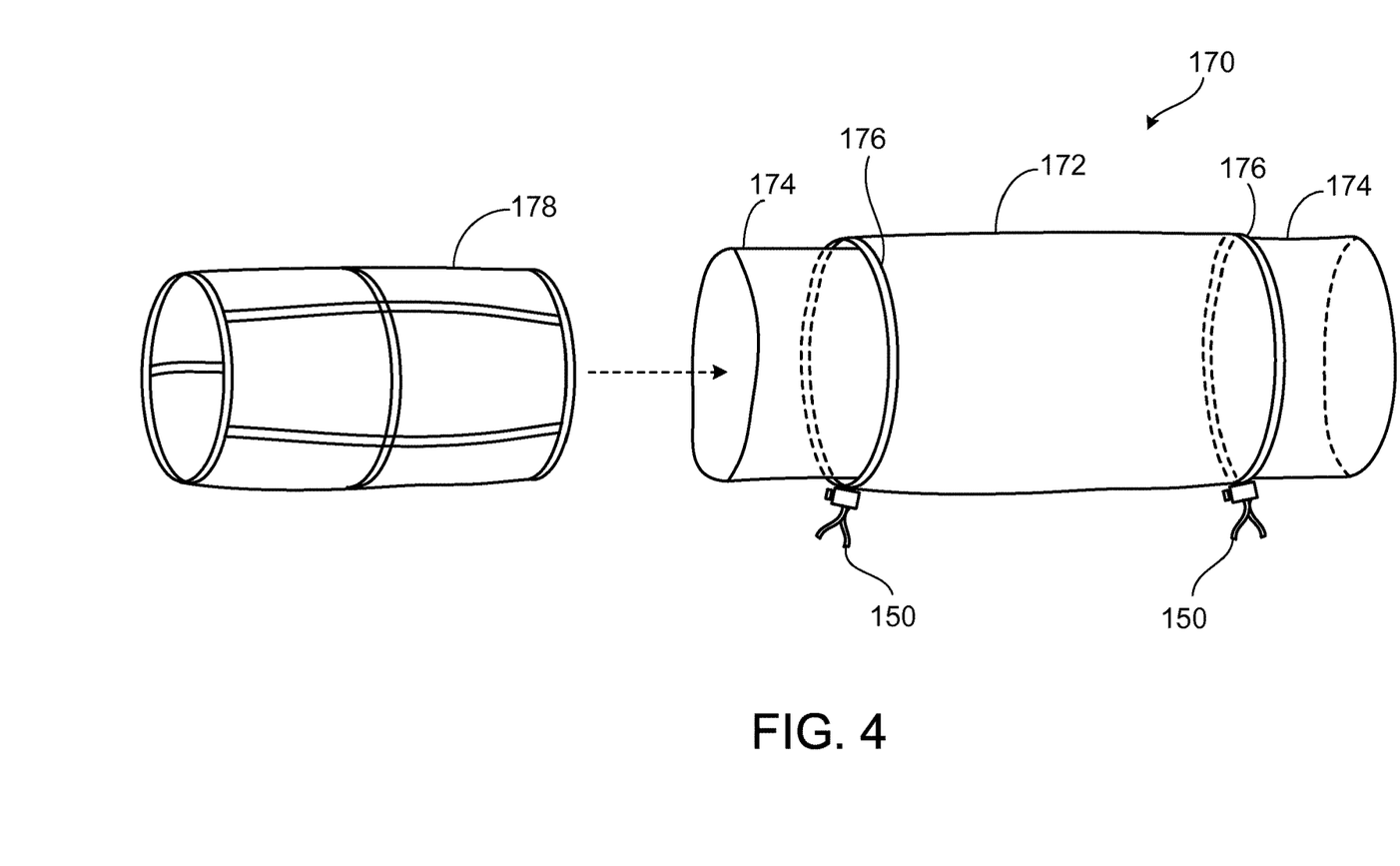

FIG. 4 shows an example low-humidity sleeve 170 that has a moisture impermeable outer shell 172 and a moisture permeable inner lining 174. The outer shell 172 has a generally tubular shape. One half of the inner liner 174 is sewn to each end 176 of the outer shell 172. A strip of desiccant packets 178, which can include silica gel or other suitable desiccating agent, is sewn into a cylinder. Compared to the strip of desiccant packets 168 of FIG. 3, the cylindrically shaped assembly of desiccant packets 178 may have less movement within the sleeve 170, which results in less bunching. Drawstrings 150 can be pulled tight to close the openings at the ends of the sleeve 170 to maximize the dehumidifying effect of the desiccant.

To use the low-humidity sleeve 170, the two sections of inner liner 174 are pulled out, the cylindrically shaped assembly of desiccant packets 178 is placed inside the outer shell 172, and the two sections of inner liner 174 are folded in to hold the desiccant packets 178 in place.

The moisture permeable inner liner 174 allows moisture in the sleeve 170 to permeate to and be adsorbed by the desiccant in the desiccant packets 178. The moisture impermeable outer shell 172 prevents outside atmospheric moisture from entering the sleeve 170 to form and maintain a low humidity environment in the region about the bone joint.

Figure 5A:
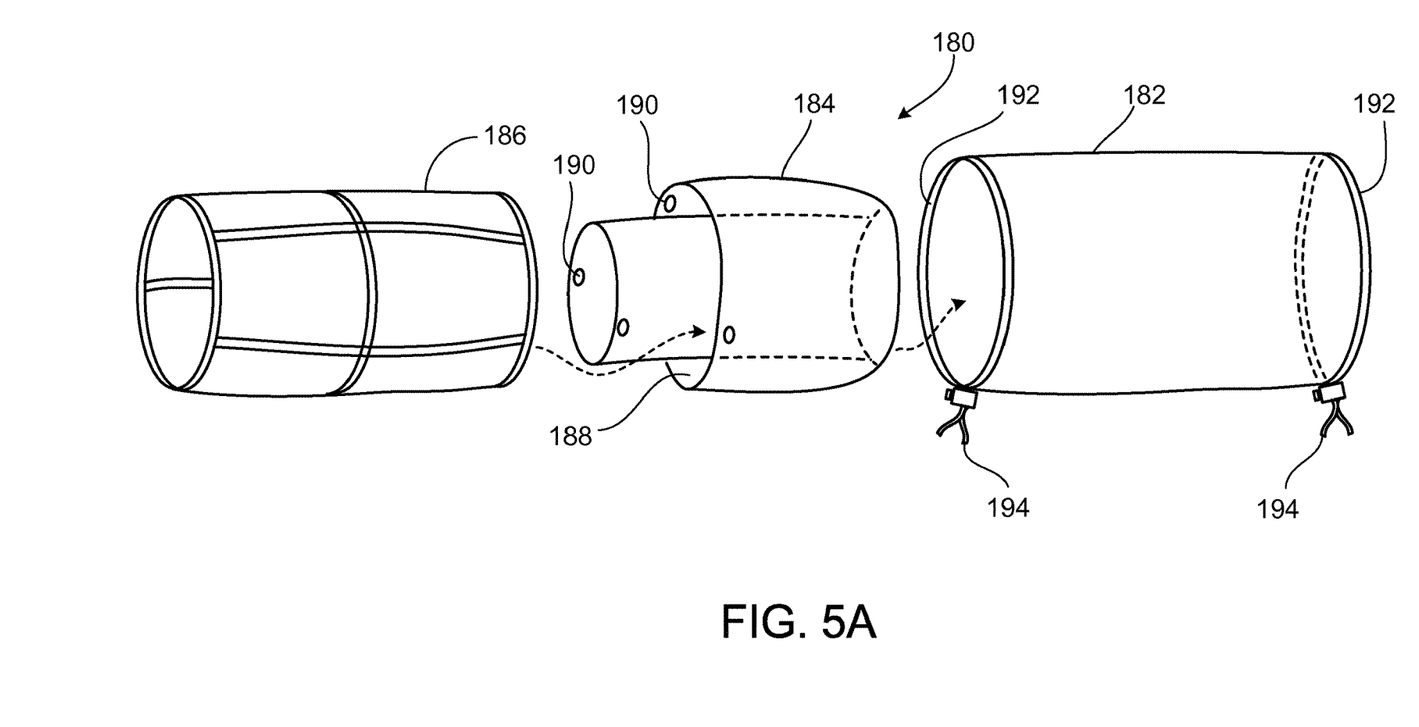

FIG. 5A shows an example low-humidity sleeve 180 that has a moisture impermeable outer shell 182 and a moisture permeable soft inner liner 184. The outer shell 182 is made into a tubular shape, and when worn over a bone joint, it defines a therapy region about the bone joint. Drawstrings 194 are provided at the ends 192 of the outer shell 182 for tightening the openings at the ends 192.

The soft inner liner 184 can be separated from the outer shell 182. In some implementations, the inner liner 184 has a tubular shape and a length between one to two times the tube length of the outer shell 182. The tubular shaped inner liner 184 is folded in half to form an open-ended tubular compartment 188 to accommodate a tubular shaped assembly of desiccant packets 186. Fasteners, such as snaps 190 or cooperating hook-and-loop-type fasteners, are installed at the ends of the inner liner tube 184 to restrict the desiccant packet tube 186 from shifting or falling out of the tubular compartment 188.

In this document, when an outer shell (or inner liner) is described as having a tubular shape, it does not mean that the outer shell (or inner liner) rigidly maintains the tubular shape. The outer shell (or inner liner) can be made of a fabric that may collapse when not being worn on the user. Thus, saying that the outer shell (or inner liner) has a tubular shape means that the outer shell (or inner liner) generally has a tubular shape when being worn on the user or when the outer shell (or inner liner) is expanded. The outer shell (or inner liner) can be flexible and may change shape to conform to the shape of the user's limb portion covered by the sleeve.

To use the low-humidity sleeve 180, the desiccant packet 186 is placed in the tubular compartment 188 formed by the inner liner 184 and the fasteners 190 act to keep the desiccant packets in place. The combination of the inner liner 184 and the desiccant packet 186 is pulled over the afflicted bone joint (e.g., knee, elbow, or hand joint), and the outer shell 182 is pulled over the outside of the inner liner assembly. One or more closure elements, such as elastic drawstrings 194 or straps, engage about the wearer's limb above and below the joint to provide a low-humidity environment in the region about the afflicted bone joint. The closure element may include an axial closure element releasably joining opposed, axially-extending edge regions of the sleeve 180 for securing the outer shell 182 in engagement about the body limb. The axial closure element can be, for example, zippers or hook-and-loop type fasteners.

For example, when the low-humidity sleeve 180 is applied to a knee, the one or more closure elements engaged about the wearer's upper leg and lower leg. When the low-humidity sleeve 180 is applied to an elbow, the one or more closure elements engaged about the wearer's upper arm and lower arm.

When the low-humidity sleeve 180 is used to alleviate hand pain, one end of the sleeve 180 can be completely tightened to close the opening. This two-part sleeve assembly is convenient to put on and take off. The desiccant packets can be removed daily for regeneration to maximize the water-adsorption capability of the desiccant.

Figure 5B:
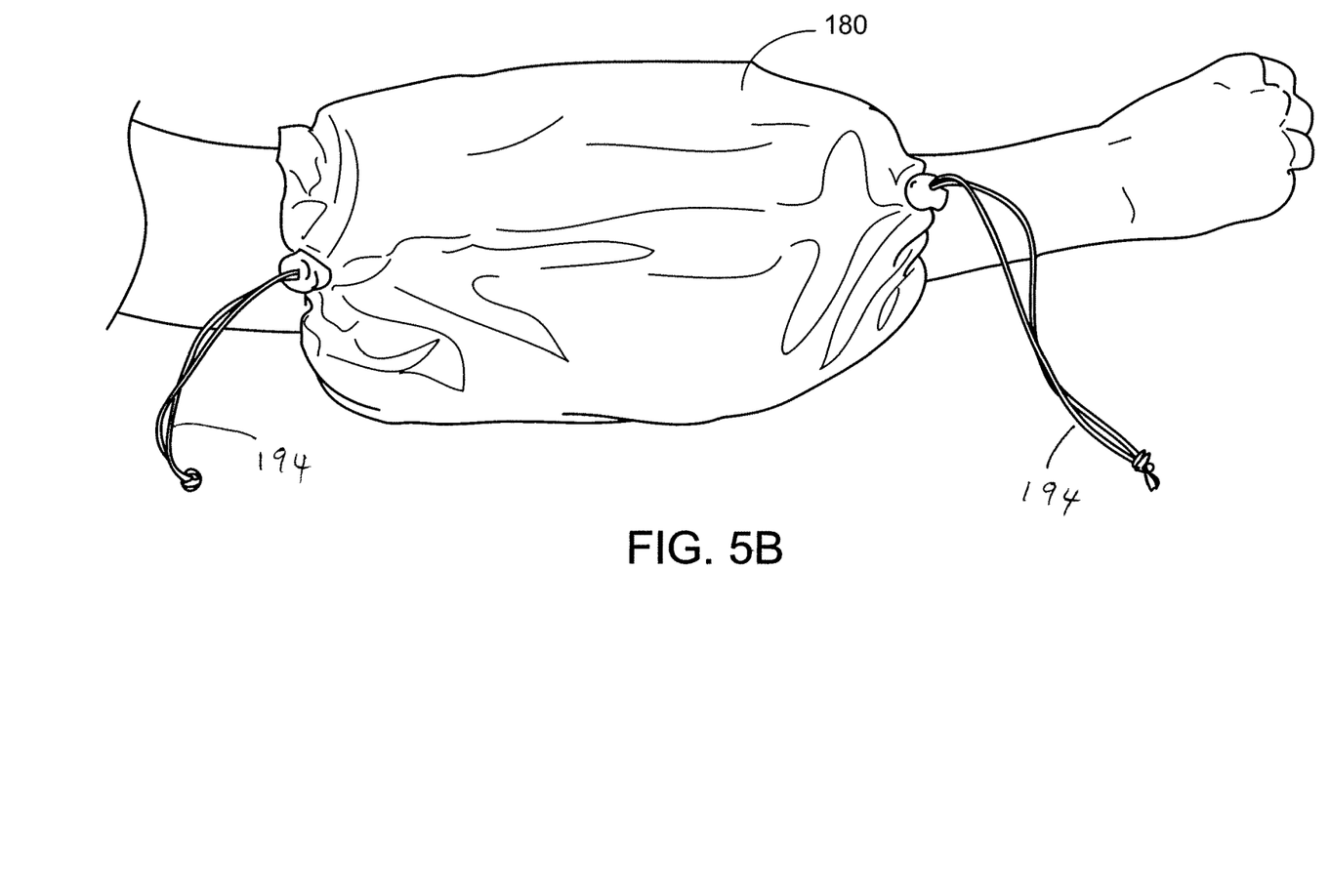
FIG. 5B shows a low-humidity sleeve being worn over an elbow joint.

FIG. 5B shows the low-humidity sleeve 180 being applied to an elbow joint. After the sleeve 180 is pulled over the elbow joint, drawstrings 194 at both ends of the sleeve 180 are tightened to provide a closed low-humidity environment in the region about the elbow joint. This may provide relief for arthritis pain at the elbow joint.

Figure 6:
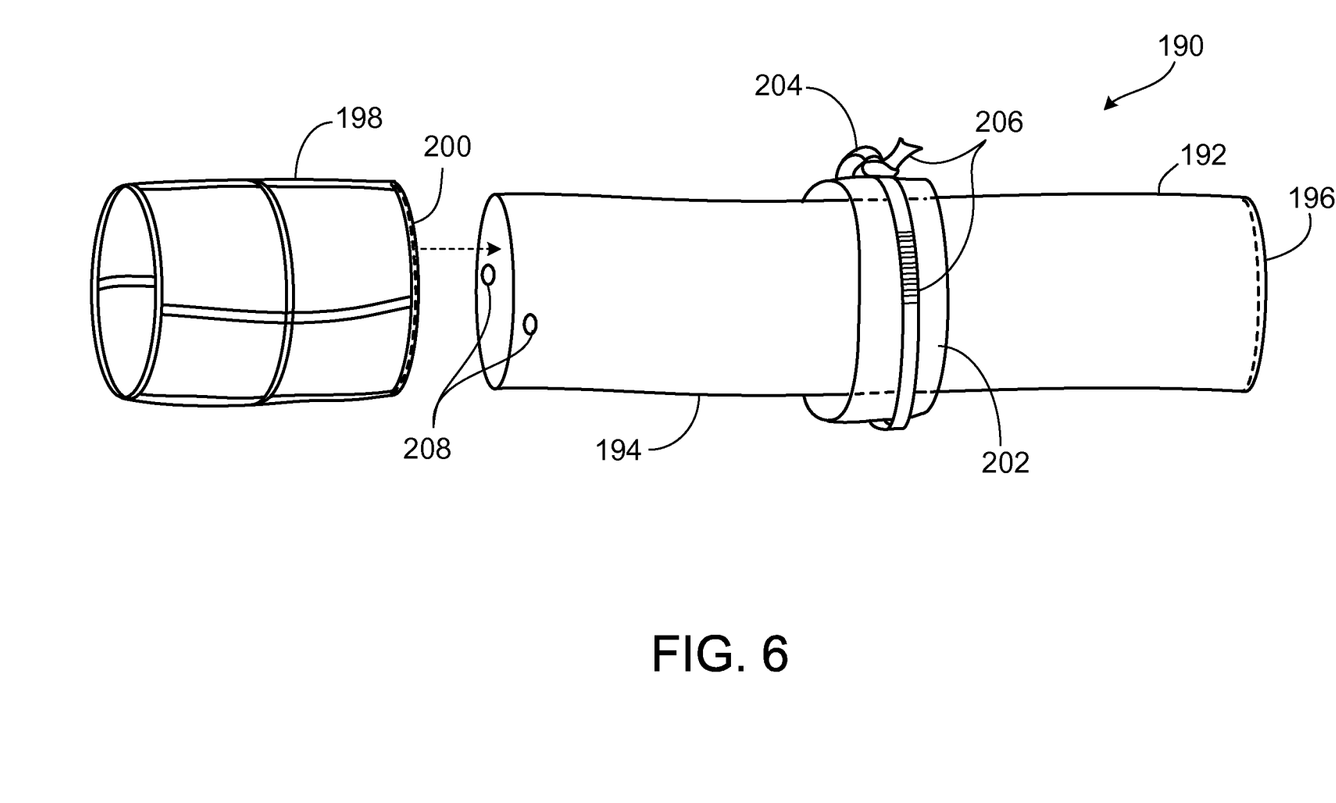
FIG. 6 shows an example low-humidity mitten (with one end open).

FIG. 6 shows an example low-humidity sleeve 190 that can provide a low-humidity environment for the hand or foot. The sleeve 190 has a moisture impermeable outer shell 192 and a moisture permeable soft inner liner 194. One end of the outer shell 192 is sewn up to form a closed end 196. A closure strap 204 having cooperating hook-and-loop-type fasteners 206 is provided at another end 202 of the outer shell 192. The sleeve 190 includes a desiccant packet 198 having one end 200 sewn up to form a bag-like pouch.

When using the low-humidity sleeve 190, the desiccant pouch 198 is inserted into the outer shell 192 with the inner liner 194 pulled out. After the desiccant pouch 198 is placed snugly inside the outer shell 192, the inner liner 194 is folded inside to cover the desiccant pouch 198 and form a soft liner for the user's hand. Fasteners, such as snaps 208, are provided at the end of the inner liner 194 to close the opening of the inner liner 194 to restrict the desiccant pouch 198 from falling out of the sleeve 190. The closure strap 204 is wrapped around the user's wrist (or ankle) and tightened to form a therapy region about the hand and wrist (or foot and ankle) that is in relative isolation from the external environment.

The moisture permeable inner liner 194 allows moisture in the sleeve 190 to permeate to and be adsorbed by the desiccant in the desiccant pouch 198. The moisture impermeable outer shell 192 prevents outside atmospheric moisture from entering the sleeve 190, which enhances the effect of the low humidity environment in the vicinity of the hand or foot.

Figure 7:
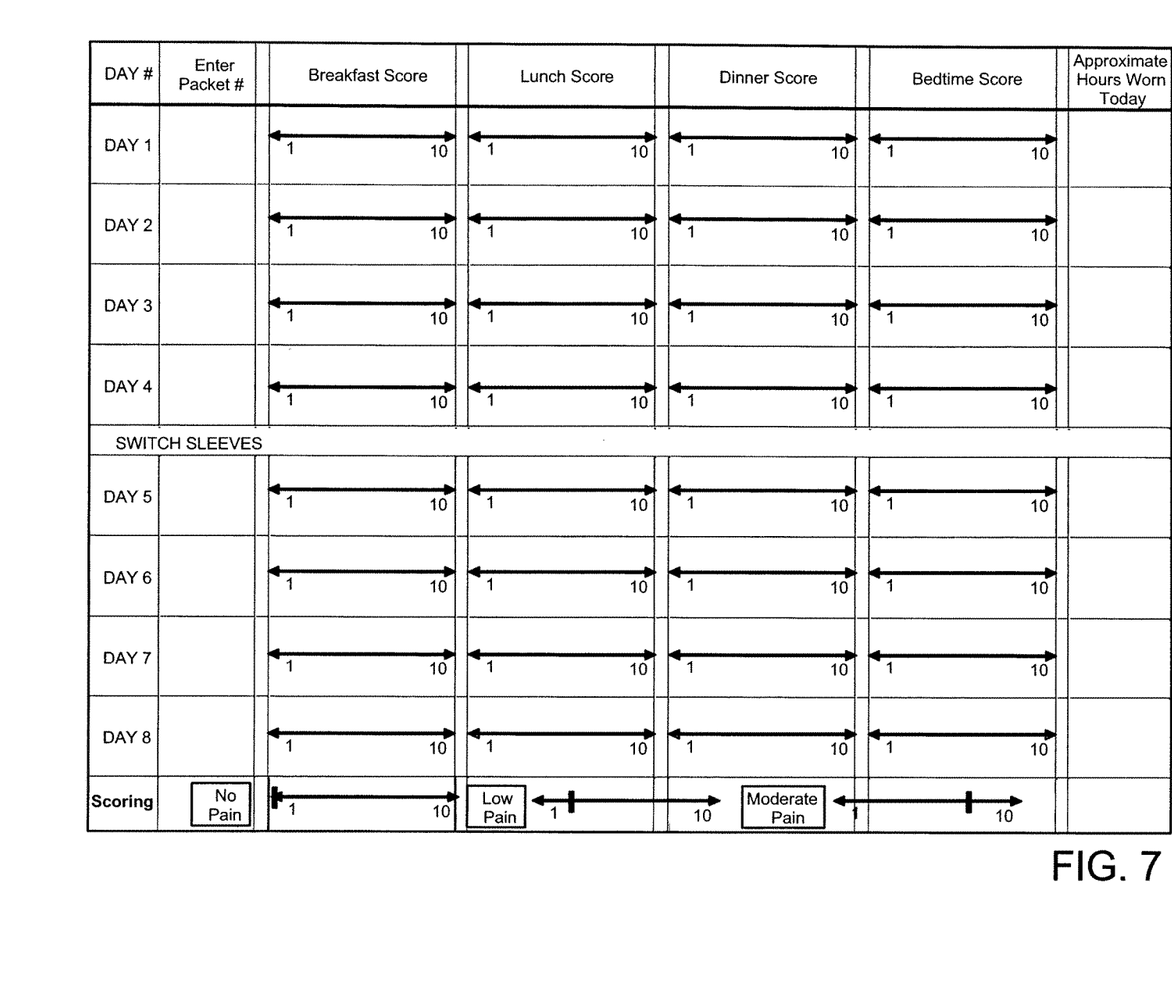
FIG. 7 is an example data sheet having visual analog scales.

Mitts that are similar to the low-humidity sleeve 190 shown in FIG. 6 were used in clinical tests on eight patients having arthritis pain. Each patient was given two mitts, one mitt having a silica gel packet pouch (referred to as the "active mitt"), the other mitt having a placebo packet pouch filled with sand (referred to as the "placebo mitt"). The patients were asked to use the active and placebo mitts as much as possible for a week, and they were told that the two mitts had different desiccant materials that were being evaluated. Each patient was instructed on the correct way to use the Visual Analog Scale (VAS) to record pain level on data sheets shown in FIG. 7. The pain levels were recorded on a scale from 0 to 10.

FIGS. 8A to 8H show the test results derived from the data sheets collected from the eight patients. Data representing pain levels associated with use of the active mitt are represented by circled dots, and data representing pain levels associated with use of the placebo mitt are represented by dots.

Figure 8A:
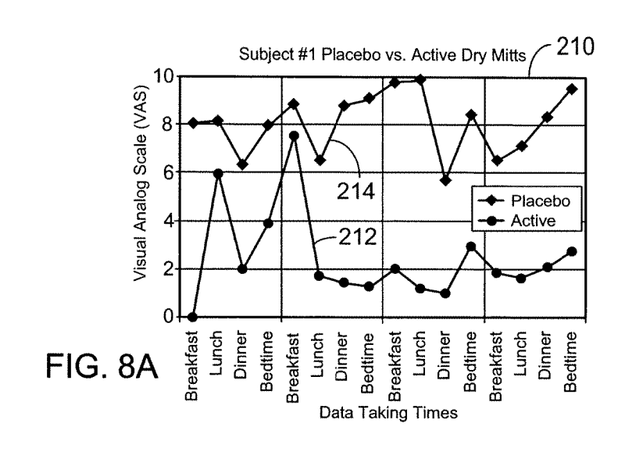
FIGS. 8A to 8H are graphs showing test results.

FIG. 8A is a graph 210 showing data associated with patient #1. A line 212 represents pain levels at various times (e.g., breakfast, lunch, dinner, bedtime) over a period of four days during which the active mitt was used, and a line 214 represents pain levels at various times over a period of four days during which the placebo mitt was used. Comparing lines 212 and 214, it can be seen that use of the active mitt resulted in lower pain levels.

Figure 8B:
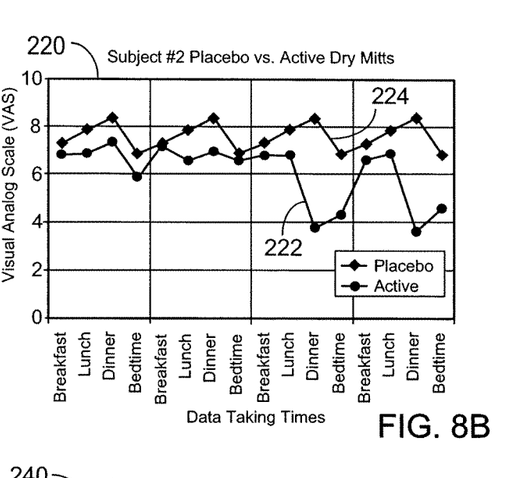

FIG. 8B is a graph 220 showing data associated with patient #2. A line 222 represents pain levels at various time periods during which the active mitt was used, and a line 224 represents pain levels at various time periods during which the placebo mitt was used. Comparing lines 222 and 224, it can be seen that use of the active mitt resulted in lower pain levels, especially for the third and fourth days.

Figure 8C:
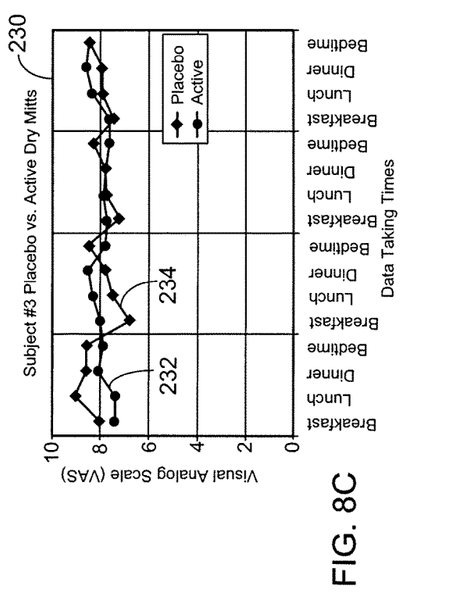

FIG. 8C is a graph 230 showing data associated with patient #3. A line 232 represents pain levels at various time periods during which the active mitt was used, and a line 234 represents pain levels at various time periods during which the placebo mitt was used. Lines 232 and 234 show little correlation between pain level and use of the active and placebo mitts.

Figure 8D:
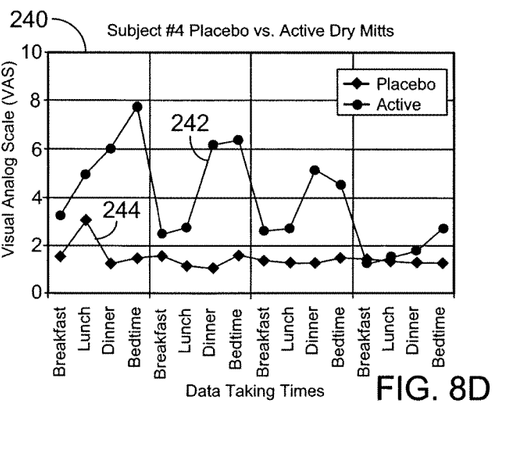

FIG. 8D is a graph 240 showing data associated with patient #4. A line 242 represents pain levels at various time periods during which the active mitt was used, and a line 244 represents pain levels at various time periods during which the placebo mitt was used. Patient #4 used the active mitt during sleeping hours. Line 242 shows a significant pain reduction overnight, as indicated by the lower pain levels during breakfast time compared with the pain levels at bedtime during a previous night. For patient #4, using the placebo mitt resulted in a lower pain level. It is unclear if the lower pain level associated with the placebo mitt was due to weather or other environmental effects.

Figure 8E:
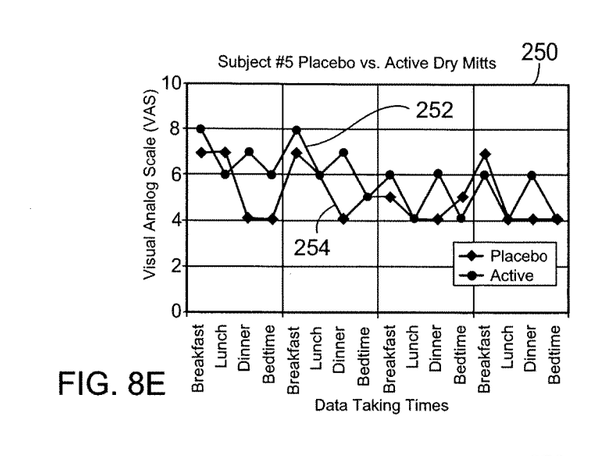

FIG. 8E is a graph 250 showing data associated with patient #5. A line 252 represents pain levels at various time periods during which the active mitt was used, and a line 254 represents pain levels at various time periods during which the placebo mitt was used. Lines 252 and 254 show little correlation between pain level and use of the active and placebo mitts.

Figure 8F:
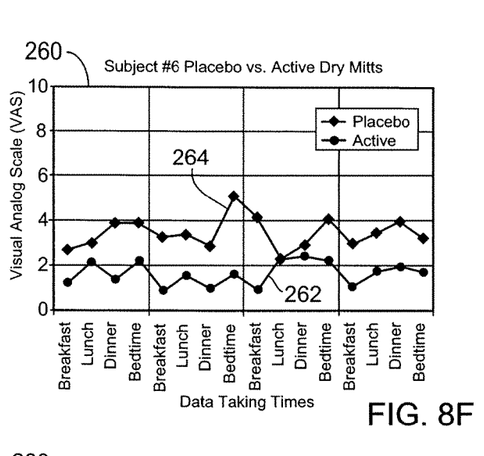

FIG. 8F is a graph 260 showing data associated with patient #6. A line 262 represents pain levels at various time periods during which the active mitt was used, and a line 264 represents pain levels at various time periods during which the placebo mitt was used. Lines 262 and 264 show that consistent lower pain levels were associated with the active mitt compared to the placebo mitt.

Figure 8G:
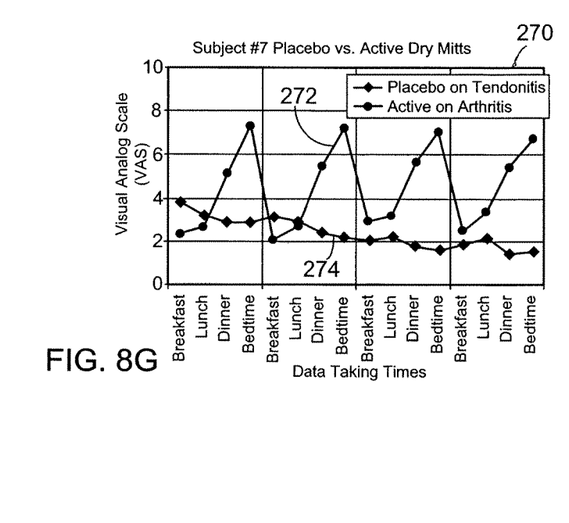

FIG. 8G is a graph 270 showing data associated with patient #7. A line 272 represents pain levels at various time periods during which the active mitt was used, and a line 274 represents pain levels at various time periods during which the placebo mitt was used. The active mitt was used on the left hand, afflicted with arthritis, during sleeping hours. Line 272 shows significant pain reduction overnight. The placebo mitt was used on the right hand with tendonitis and so the data represented by line 274 cannot be used for comparison with the active mitt.

Figure 8H:
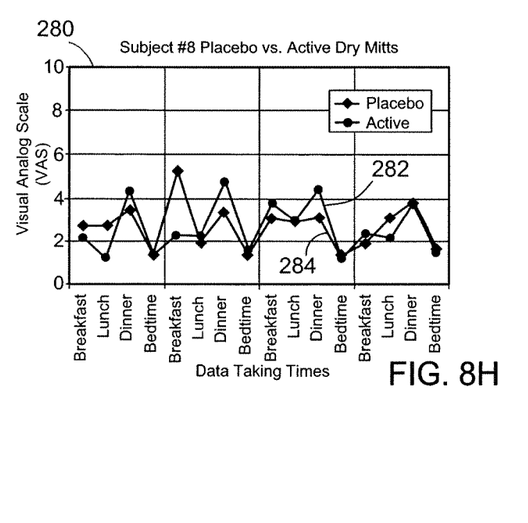

FIG. 8H is a graph 280 showing data associated with patient #8. A line 282 represents pain levels at various time periods during which the active mitt was used, and a line 284 represents pain levels at various time periods during which the placebo mitt was used. Lines 282 and 284 show little correlation between the pain level and the use of the active and placebo mitts.

The graphs in FIGS. 8A to 8H show that for some of the patients, wearing the mitt with silica gel resulted in reduced pain levels.

Although various implementations have been described, other implementations can also be used. For example, instead of using a mitten shape as shown in FIG. 1, a glove with five compartments for five fingers can be used. The shapes and dimensions of the low-humidity mittens and low-humidity sleeves and the materials used for the outer shell and inner liner can be different from those described above. Non-woven fabric or nano-fabric can be used to form all or part of the outer shell or inner liner. In some implementations, a water impermeable and breathable fabric (e.g., Gore-Tex®, available from W. L. Gore & Associates, Inc., Elkton, Md.) can be used for the outer shell. Although the breathable fabric may allow some atmospheric water vapor to enter the low-humidity mitten or sleeve when the mitten or sleeve has humidity lower than the outside humidity, the desiccative agent will adsorb most of the water vapor to maintain a low-humidity therapy region. Using a breathable fabric may be advantageous for people who sweat considerably when the low-humidity mitten or sleeve is initially put on so that some of the perspiration can evaporate through the breathable fabric instead of being entirely adsorbed by the desiccative agent. When breathable material is used for the outer shell, because atmospheric water vapor is allowed to enter the closed environment, the lowest humidity level achieved may not be as low as that achieved with an absolutely impermeable outer shell. Also, allowing leakage of atmospheric water vapor in to the desiccant may shorten time over which low humidity relief is produced for the arthritis victim.

Materials other than silica gel can be used as the desiccant, e.g., Natrasorb® desiccant materials, available from Multisorb Technologies, Buffalo, N.Y. For the low-humidity sleeves shown in FIGS. 2A and 3-6, the moisture permeable inner liners can be sewn to the outer shell to form quilted sections each containing desiccant, thereby forming integrated sleeves that are easy to use. To regenerate the silica gel, the user can turn the sleeve inside-out and place the sleeve in a clothes dryer, convection oven, microwave oven, or other device which can be used to accomplish the desiccant regeneration process. A low-humidity device can have a general shape of a bootie or sock and be applied to the joints of the toes, foot and/or ankle. Straps or drawstrings can be used to tighten the end of the low-humidity device about a wearer's ankle or calf. The invention may also be applied to other bone joints of a wearer's body, e.g. shoulder joints or hip joints. Closure elements other than those described above can be used. Other embodiments are within the scope of the following claims.

What is claimed is:

1. A self-contained appliance for passive therapy of arthritis discomfort in a bone joint, comprising:
   a bone joint-encompassing element comprising:
      a sleeve-shaped body defining an inner volume, and defining apertures at opposite ends of the sleeve-shaped body, such that the inner volume of the sleeve-shaped body is exposed to an external environment through the apertures, the sleeve-shaped body comprising:
         an outer shell comprising a moisture impermeable and water vapor impermeable barrier material,
         a tubular-shaped inner liner received and extending within the outer shell and comprising a moisture permeable material and configured to define a therapy region for receiving therewithin one or more bone joints, the inner liner being separable from the outer shell and folded upon itself in a longitudinal axial direction of the inner liner to form a tubular compartment having an open end and a closed end, and
         a tubular-shaped assembly defining apertures at opposite ends of the tubular-shaped assembly, the tubular-shaped assembly received and extending within the tubular compartment in the longitudinal axial direction of the inner liner, wherein one or more containments of the tubular-shaped assembly contain packets including a desiccative agent, the desiccative agent comprising a material that adsorbs or absorbs water vapor, thereby to reduce humidity in the therapy region, and
   two or more closure elements configured to seal each of the apertures of the sleeve-shaped body, whereby the therapy region is isolated from moisture and water vapor of the external environment.

2. The self-contained appliance for passive therapy of arthritis discomfort in a bone joint of claim 1, wherein the two or more closure elements are associated with said bone joint-encompassing element and configured to engage about a body limb associated with the one or more bone joints.

3. The self-contained appliance for passive therapy of arthritis discomfort in a bone joint of claim 2, wherein:
   the one or more bone joints is a bone joint of the body limb; and
   said two or more closure elements associated with the bone joint-encompassing element are configured to engage about the body limb above and below the bone joint.

4. The self-contained appliance for passive therapy of arthritis discomfort in a bone joint of claim 3, wherein:
   the bone joint of the body limb is a knee; and
   said two or more closure elements are configured to engage about a wearer's upper leg and lower leg.

5. The self-contained appliance for passive therapy of arthritis discomfort in a bone joint of claim 3, wherein:
   the bone joint of the body limb is an elbow; and
   said two or more closure elements are configured to engage about a wearer's upper arm and lower arm.

6. The self-contained appliance for passive therapy of arthritis discomfort in a bone joint of claim 2, wherein the two or more closure elements comprise an axial closure element releasably joining opposed, axially-extending edge regions of a sleeve for securing said bone joint-encompassing element in engagement about the body limb.

7. The self-contained appliance for passive therapy of arthritis discomfort in a bone joint of claim 6, wherein the axial closure element is selected from a group consisting of zippers and hook-and-loop type fasteners.

8. The self-contained appliance for passive therapy of arthritis discomfort in a bone joint of claim 1, wherein the two or more closure elements comprise a drawstring that reduces a size of the apertures of the bone joint-encompassing element when drawn.

9. The self-contained appliance for passive therapy of arthritis discomfort in a bone joint of claim 1, wherein the desiccative agent comprises silica gel.

10. The self-contained appliance for passive therapy of arthritis discomfort in a bone joint of claim 1, wherein the moisture impermeable and water vapor impermeable barrier material comprises a thermal insulator to retain heat within the appliance.

11. The self-contained appliance for passive therapy of arthritis discomfort in a bone joint of claim 1, wherein:
   the one or more bone joints is a bone joint of a body limb; and
   the two or more closure elements are associated with the bone joint-encompassing element and are configured to engage about the body limb above and below the bone joint.

12. The self-contained appliance for passive therapy of arthritis discomfort in a bone joint of claim 1, wherein one of the closure elements is fixed.

13. The self-contained appliance for passive therapy of arthritis discomfort in a bone joint of claim 1, wherein the tubular-shaped assembly removably resides within the tubular compartment such that the tubular-shaped assembly can be removed via the open end of the tubular compartment.

14. A method for passive therapy of arthritis discomfort in a bone joint, the method comprising the steps of:
enclosing one or more bone joints within a therapy region of a self-contained treatment appliance, the therapy region being defined by a bone joint-encompassing element that comprises a sleeve-shaped body defining an inner volume, and defining apertures at opposite ends of the sleeve-shaped body, such that the inner volume of the sleeve-shaped body is exposed to an external environment through the apertures, the sleeve-shaped body comprising:
an outer shell comprising a moisture impermeable and water vapor impermeable barrier material,
a tubular-shaped inner liner received and extending within the outer shell and comprising a moisture permeable material, the inner liner being separable from the outer shell and folded upon itself in a longitudinal axial direction of the inner liner to form a tubular compartment having an open end and a closed end, and
a tubular-shaped assembly defining apertures at opposite ends of the tubular-shaped assembly, the tubular-shaped assembly received and extending within the tubular compartment in the longitudinal axial direction of the inner liner, the tubular-shaped assembly comprising one or more containments;
placing packets including a desiccative agent within the one or more containments of the tubular-shaped assembly, the desiccative agent comprising a material that adsorbs or absorbs water vapor, thereby to reduce humidity in the therapy region;
securing two or more closure elements in engagement about a body limb associated with the one or more bone joints, the two or more closure elements configured for sealing each of apertures of the sleeve-shaped body, whereby the therapy region is isolated from moisture and water vapor of the external environment; and
continuing the therapy for a period of time.

15. A self-contained appliance for passive therapy of arthritis discomfort in a bone joint, comprising:
a bone joint-encompassing element comprising:
a sleeve-shaped body defining an inner volume, and defining an aperture at an end of the of the sleeve-shaped body, such that the inner volume of the sleeve-shaped body is exposed to an external environment through the aperture, the sleeve-shaped body comprising:
an outer shell comprising a moisture impermeable and water vapor impermeable barrier material,
a tubular-shaped inner liner received and extending within the outer shell and comprising a moisture permeable material and configured to define a therapy region for receiving therewithin one or more bone joints, the inner liner being separable from the outer shell and folded upon itself in a longitudinal axial direction of the inner liner to form a tubular compartment having an open end and a closed end, and
a tubular-shaped assembly defining apertures at opposite ends of the tubular-shaped assembly, the tubular-shaped assembly received and extending within the tubular compartment in the longitudinal axial direction of the inner liner, wherein one or more containments of the tubular-shaped assembly contain packets including a desiccative agent, the desiccative agent comprising a material that adsorbs or absorbs water vapor, thereby to reduce humidity in the therapy region, and
a closure element configured to seal the aperture of the sleeve-shaped body, whereby the therapy region is isolated from moisture and water vapor of the external environment.

16. The self-contained appliance for passive therapy of arthritis discomfort in a bone joint of claim 15, wherein:
the one or more bone joints are joints of the fingers, hand or wrist; and
the closure element is associated with the bone joint-encompassing element and is configured to engage about a wearer's wrist or forearm.

17. The self-contained appliance for passive therapy of arthritis discomfort in a bone joint of claim 15, wherein:
the one or more bone joints are joints of the toes, foot or ankle; and
the closure element is associated with the bone joint-encompassing element and is configured to engage about a wearer's ankle or calf.

18. The self-contained appliance for passive therapy of arthritis discomfort in a bone joint of claim 15, wherein the closure element is associated with said bone joint-encompassing element and configured to engage about a body limb associated with the one or more bone joints.

19. The self-contained appliance for passive therapy of arthritis discomfort in a bone joint of claim 18, wherein:
the one or more bone joints are joints of the fingers, hand or wrist; and
the closure element associated with the bone joint-encompassing element is configured to engage about a wearer's wrist or forearm.

20. The self-contained appliance for passive therapy of arthritis discomfort in a bone joint of claim 18, wherein:
the one or more bone joints are joints of the toes, foot or ankle; and
the closure element associated with the bone joint-encompassing element is configured to engage about a wearer's ankle or calf.

* * * * *

UNITED STATES PATENT AND TRADEMARK OFFICE
CERTIFICATE OF CORRECTION

PATENT NO. : 10,251,775 B2
APPLICATION NO. : 12/252001
DATED : April 9, 2019
INVENTOR(S) : Mary Lucia Leone Hedberg Page 1 of 1

It is certified that error appears in the above-identified patent and that said Letters Patent is hereby corrected as shown below:

In the Specification

Column 1, Line 7, delete "60/999,003" and insert -- 60/999,003, --, therefor.

In the Claims

Column 11, Line 43, in Claim 14, before "apertures" insert -- the --.

Column 11, Line 51, in Claim 15, delete "of the of the" and insert -- of the --, therefor.

Signed and Sealed this
Twenty-fifth Day of June, 2019

Andrei Iancu
*Director of the United States Patent and Trademark Office*